US00PP19406P2

(12) United States Plant Patent

Mehring-Lemper

(10) Patent No.: US PP19,406 P2

(45) Date of Patent: Nov. 4, 2008

(54) *AGASTACHE* PLANT NAMED 'AGA 204'

(50) Latin Name: *Agastache mexicana*
Varietal Denomination: AGA 204

(75) Inventor: Manfred Mehring-Lemper, Hann. Münden (DE)

(73) Assignee: Ernst Benary Samen Zucht GmbH of Hann, Münden (DE)

( * ) Notice: Subject to any disclaimer, the term of this patent is extended or adjusted under 35 U.S.C. 154(b) by 0 days.

(21) Appl. No.: 11/978,096

(22) Filed: Oct. 25, 2007

(51) Int. Cl.
*A01H 5/00* (2006.01)

(52) U.S. Cl. ..... Plt./399

(58) Field of Classification Search ..... Plt./399
See application file for complete search history.

*Primary Examiner*—Annette H Para
(74) *Attorney, Agent, or Firm*—C. A. Whealy

(57) ABSTRACT

A new and distinct cultivar of *Agastache* plant named 'AGA 204', characterized by its compact and upright plant habit; freely branching habit; moderately vigorous growth habit; long inflorescences with dark pink-colored flowers; freely and continuous flowering habit; and good garden performance.

1 Drawing Sheet

Botanical designation: *Agastache mexicana.*
Cultivar denomination: 'AGA 204'.

BACKGROUND OF THE INVENTION

The present invention relates to a new and distinct cultivar of *Agastache,* botanically known as *Agastache mexicana* and hereinafter referred to by the name 'AGA 204'.

The new *Agastache* is a product of a planned breeding program conducted by the Inventor in Hann. Münden, Germany. The objective of the breeding program was to create new *Agastache* cultivars with large and dense inflorescences and attractive flower coloration.

The new *Agastache* originated from an open-pollination during the summer of 2003 in Hann. Münden, Germany, of an unnamed selection of *Agastache mexicana,* not patented, as the female, or seed, parent with an unknown selection of *Agastache mexicana* as the male, or pollen, parent. The new *Agastache* was discovered and selected by the Inventor as a single flowering plant within the progeny of the stated open-pollination in a controlled environment in Hann, Münden, Germany during the summer of 2004.

Asexual reproduction of the new *Agastache* by vegetative cuttings in a controlled environment in Hann. Münden, Germany during the winter of 2004, has shown that the unique features of this new *Agastache* are stable and reproduced true to type in successive generations.

SUMMARY OF THE INVENTION

The cultivar AGA 204 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'AGA 204'. These characteristics in combination distinguish 'AGA 204' as a new and distinct cultivar of *Agastache:*

1. Compact and upright plant habit.
2. Freely branching habit.

3. Moderately vigorous growth habit.
4. Long inflorescences with dark pink-colored flowers.
5. Freely and continuous flowering habit.
6. Good garden performance.

Compared to plants of the female parent selection, plants of the new *Agastache* are more compact and differ in flower coloration.

Plants of the new *Agastache* can also be compared to plants of the cultivar Acapulco Rose-Red, not patented. In side-by-side comparisons conducted in Hann, Müden, Germany, plants of the new *Agastache* and the cultivar Acapulco Rose-Red differed in the following characteristics:

1. Plants of the new *Agastache* had lighter-colored flowers buds than plants of the cultivar Acapulco Rose-Red.
2. Plants of the new *Agastache* had lighter-colored flowers than plants of the cultivar Acapulco Rose-Red.

BRIEF DESCRIPTION OF THE PHOTOGRAPHS

The accompanying colored photographs illustrate the overall appearance of the new *Agastache,* showing the colors as true as it is reasonably possible to obtain in colored reproductions of this type. Colors in the photographs may differ slightly from the color values cited in the detailed botanical description which accurately describe the colors of the new *Agastache.*

The photograph at the bottom of the sheet comprises a side perspective view of typical rooted young plants of 'AGA 204' grown in a container.

The photograph at the top of the sheet is a close-up view of a typical inflorescence of 'AGA 204'.

DETAILED BOTANICAL DESCRIPTION

The aforementioned photographs and following observations, measurements and values describe plants grown in Litchfield, Mich. during the summer and under commercial practice in a polyethylene-covered greenhouse. During the production of the plants, day temperatures ranged from 20° C. to 24° C. and night temperatures ranged from 16° C. to 18° C. After planting, plants were pinched one time. Plants had been growing for about six weeks when the photographs and description were taken. In the following description, color references are made to The Royal Horticultural Society Colour Chart, 1995 Edition, except where general terms of ordinary dictionary significance are used.

Botanical classification: *Agastache mexicana* cultivar AGA 204.

Parentage:

*Female, or seed, parent.*—Unnamed selection of *Agastache mexicana,* not patented.

*Male, or pollen, parent.*—Unknown selection of *Agastache mexicana,* not patented.

Propagation:

*Type.*—By vegetative cuttings.

*Time to initiate roots, summer.*—About 15 to 20 days at 22° C.

*Time to initiate roots, winter.*—About three to four weeks at 20° C.

*Time to produce a rooted young plant roots, summers.*—About four weeks at 20° C.

*Time to produce a rooted young plant roots, winter.*—About five weeks at 20° C.

*Root description.*—Fine, fibrous; 158C in color.

Plant description:

*Plant form/habit.*—Compact and upright plant habit; moderately vigorous growth habit. Freely branching habit with about four lateral branches; pinching enhances branching potential.

*Plant height.*—About 15 cm.

*Plant width (spread).*—About 14 cm.

*Lateral branches.*—Length: About 5.5 cm. Diameter: About 2 mm. Internode length: About 2 cm. Strength: Strong. Texture: Pubescent. Color: 146B.

Foliage description:

*Arrangement.*—Opposite, simple.

*Length.*—About 3 cm.

*Width.*—About 2.5 cm.

*Shape.*—Ovate to deltoid.

*Apex.*—Broadly acute.

*Base.*—Obtuse with cordate tendencies.

*Margin.*—Crenate.

*Texture, upper surface.*—Smooth, glabrous.

*Texture, lower surface.*—Pubescent.

*Venation pattern.*—Pinnate; arcuate.

*Color.*—Developing leaves, upper surface: 144A. Developing leaves, lower surface: 146B. Fully expanded leaves, upper surface: 146A; venation, 146A. Fully expanded leaves, lower surface: 146B; venation, 147C.

*Petiole length.*—About 2 cm.

*Petiole diameter.*—About 1 mm.

*Petiole texture, upper and lower surfaces.*—Pubescent.

*Petiole color, upper and lower surfaces.*—146B.

Flower description:

*Flower type and habit.*—Numerous single bilabiate flowers arranged in verticillasters arranged in long terminal and axillary spikes. Individual flowers face mostly outward. Freely flowering habit with about 50 flowers and flower buds developing per terminal spike. Flowers not persistent.

*Natural flowering seasons.*—Plants flower from late June through September in the Northern Hemisphere; flowering continuous during this period.

*Inflorescence longevity on the plant.*—About one week.

*Fragrance.*—None detected.

*Inflorescence length.*—About 4.5 cm.

*Inflorescence width.*—About 4.2 cm.

*Flowers.*—Appearance: Zygomorphic; bilabiate. Length: About 2.5 cm. Diameter: About 6 mm.

*Flower buds.*—Length: About 1.8 cm. Diameter: About 3.5 mm. Shape: Obovate; curved. Color: 78D.

*Corolla.*—Petal arrangement/appearance: Bilabiate; five petals, upper two banner petals; two lateral petals and one lower lip petal; all five petals fused at base into a tubular structure. Petal lobe length: Banner petals: About 3 mm. Lateral petals: About 2 mm. Lip petal: About 5 mm. Petal lobe width: Banner petals: About 2.5 mm. Lateral petals: About 2 mm. Lip petal: About 4 mm. Petal apex: Banner and lateral petals: Rounded. Lip petal: Praemorse. Petal lobe margin, all petals: Entire. Corolla texture, inner surface: Smooth, glabrous. Corolla texture, outer surface: Pubescent. Corolla color: When opening, inner surface: 78C. When opening, outer surface: 78D. Fully opened, inner surface: 78B. Fully opened, outer surface: 78C.

*Calyx.*—Sepal quantity/arrangement: One single short calyx tube per flower of five fused sepals. Sepal length: About 1 mm. Sepal diameter: About 1 mm. Sepal shape: Lanceolate. Sepal apex: Acute. Sepal margin: Entire. Texture, inner surface: Smooth, glabrous. Texture, outer surface: Pubescent. Color, inner and outer surfaces: 148B.

*Peduncles.*—Length: About 1.2 cm. Diameter: About 1.5 mm. Strength: Strong. Angle: Erect to about 45° from vertical. Texture: Pubescent. Color: 144A.

*Pedicels.*—Length: About 3 mm. Diameter: Less than 1 mm. Strength: Strong. Angle: About 35° to 45° from peduncle axis. Texture: Pubescent. Color: 191A.

*Reproductive organs.*—Stamens: Quantity per flower: Four. Filament length: About 2.3 cm. Filament color: 78B. Anther shape: Bi-lobed. Anther length: About 1 mm. Anther color: 86A. Pollen amount: Scarce. Pollen color: 157D. Pistils: Quantity per flower: One. Pistil length: About 2.5 cm. Style length: About 2.4 mm. Style color: 75A to 75B. Stigma shape: Bi-parted. Stigma color: 71A. Ovary color: 145B.

*Seed/fruit.*—Seed nor fruit production has not been observed.

Disease/pest resistance: Plants of the new *Agastache* have not been noted to be resistant to pathogens or pests common to *Agastache.*

Garden performance: Plants of the new *Agastache* have been observed to have good garden performance and to be tolerant to rain, wind and temperatures ranging from about 0° C. to 38° C.

It is claimed:

1. A new and distinct *Agastache* and plant named 'AGA 204' as illustrated and described.

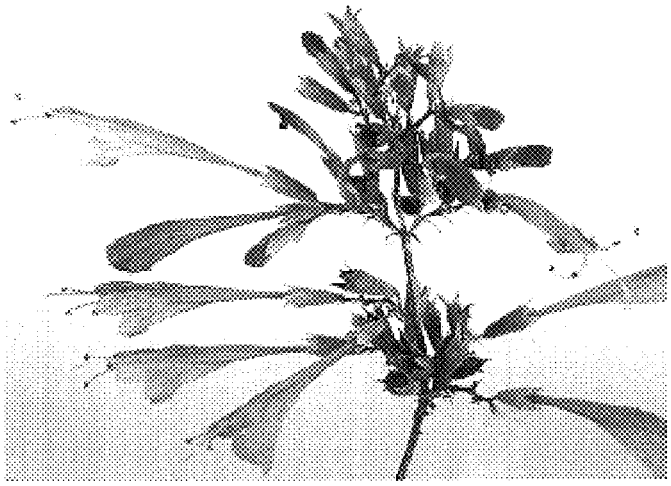
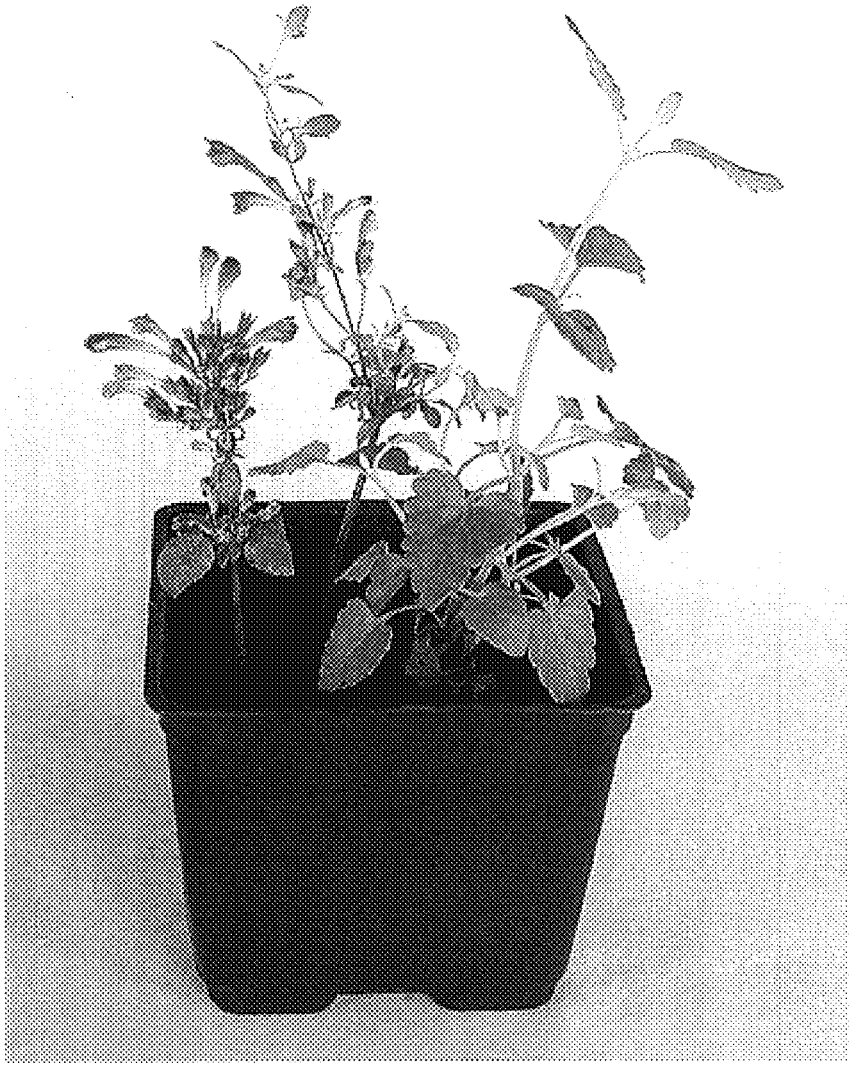

* * * * *